(12) United States Patent
Eckert et al.

(10) Patent No.: US 11,776,696 B2
(45) Date of Patent: Oct. 3, 2023

(54) SYSTEM AND METHOD FOR PROCESSING WIRELESS BACKSCATTERED SIGNAL USING ARTIFICIAL INTELLIGENCE PROCESSING FOR ACTIVITIES OF DAILY LIFE

(71) Applicant: Koko Home, Inc., Palo Alto, CA (US)

(72) Inventors: Bradley Michael Eckert, Palo Alto, CA (US); Luca Rigazio, Palo Alto, CA (US); Neal Khosla, Palo Alto, CA (US); Kiran Joshi, Palo Alto, CA (US)

(73) Assignee: Koko Home, Inc., Palo Alto, CA (US)

( * ) Notice: Subject to any disclaimer, the term of this patent is extended or adjusted under 35 U.S.C. 154(b) by 0 days.

(21) Appl. No.: 17/883,654

(22) Filed: Aug. 9, 2022

(65) Prior Publication Data

US 2022/0384047 A1 Dec. 1, 2022

Related U.S. Application Data

(63) Continuation of application No. 17/526,283, filed on Nov. 15, 2021, now Pat. No. 11,462,330, which is a
(Continued)

(51) Int. Cl.
*G16H 50/30* (2018.01)
*A61B 5/0205* (2006.01)
(Continued)

(52) U.S. Cl.
CPC .......... *G16H 50/30* (2018.01); *A61B 5/0015* (2013.01); *A61B 5/0205* (2013.01);
(Continued)

(58) Field of Classification Search
CPC .... G16H 50/30; A61B 5/0015; A61B 5/0205; A61B 5/025; A61B 5/7221; A61B 5/746;
(Continued)

(56) References Cited

U.S. PATENT DOCUMENTS 7,436,348 B2 10/2008 Nohmi
7,925,995 B2 4/2011 Krumm et al.
(Continued)

FOREIGN PATENT DOCUMENTS

CN 207869389 U 9/2018
GB 2520169 A 5/2015
(Continued)

OTHER PUBLICATIONS

Rantz et al., A New Paradigm of Technology-Enabled 'Vital Signs' for Early Detection of Health Change for Older Adults, Published Online: Nov. 26, 2014, Gerontology 2015; 61, pp. 281-290 (Year: 2014).*
(Continued)

*Primary Examiner* — Toan M Le
(74) *Attorney, Agent, or Firm* — Schwegman Lundberg & Woessner, P.A.

(57) ABSTRACT

In an example, the technique also detects and measures vital signs of each human target by continuous, non-intrusive method. In an example, the vital signs of interest include a heart rate and a respiratory rate, which can provide valuable information about the human's wellness. Additionally, the heart rate and respiratory rate can also be used to identify a particular person, if more than two target humans living in a home. Of course, there can be other variations, modifications, and alternatives.

30 Claims, 12 Drawing Sheets

Related U.S. Application Data continuation of application No. 17/244,554, filed on Apr. 29, 2021, now abandoned, which is a continuation of application No. 16/103,829, filed on Aug. 14, 2018, now Pat. No. 11,004,567.

(60) Provisional application No. 62/545,921, filed on Aug. 15, 2017.

(51) Int. Cl.
| | |
|---|---|
| *A61B 5/00* | (2006.01) |
| *G06N 5/025* | (2023.01) |
| *H04B 1/16* | (2006.01) |
| *H04B 1/04* | (2006.01) |
| *A61B 5/024* | (2006.01) |
| *A61B 5/08* | (2006.01) |
| *A61B 5/11* | (2006.01) |
| *G16H 40/60* | (2018.01) |

(52) U.S. Cl.
CPC ............ *A61B 5/7221* (2013.01); *G06N 5/025* (2013.01); *A61B 5/024* (2013.01); *A61B 5/0816* (2013.01); *A61B 5/1113* (2013.01); *A61B 5/1118* (2013.01); *A61B 5/741* (2013.01); *A61B 5/746* (2013.01); *A61B 2503/08* (2013.01); *A61B 2505/07* (2013.01); *A61B 2560/0242* (2013.01); *A61B 2562/0204* (2013.01); *A61B 2562/028* (2013.01); *A61B 2562/029* (2013.01); *A61B 2562/0219* (2013.01); *A61B 2562/0223* (2013.01); *A61B 2562/0228* (2013.01); *A61B 2562/0271* (2013.01); *G16H 40/60* (2018.01); *H04B 1/04* (2013.01); *H04B 1/16* (2013.01)

(58) Field of Classification Search
CPC .... A61B 2560/0242; A61B 2562/0219; A61B 2562/0223; A61B 5/024; G06N 5/025
See application file for complete search history.

(56) References Cited

U.S. PATENT DOCUMENTS

| | | | |
|---|---|---|---|
| 8,446,253 B2 | 5/2013 | Ramchandran et al. | |
| 8,562,526 B2 | 10/2013 | Heneghan et al. | |
| 8,606,249 B1 | 12/2013 | Goodwin | |
| 9,196,257 B2 | 11/2015 | Schultz-amling et al. | |
| 9,309,782 B2 | 4/2016 | Kareff et al. | |
| 9,311,802 B1 | 4/2016 | Chin et al. | |
| 9,319,782 B1 | 4/2016 | Crump et al. | |
| 9,807,725 B1 | 10/2017 | Vitus et al. | |
| 9,972,917 B2 | 5/2018 | Vacanti et al. | |
| 10,457,161 B2 | 10/2019 | Lu-dac et al. | |
| 10,568,565 B1 | 2/2020 | Kahn et al. | |
| 10,743,100 B1 | 8/2020 | Eckert et al. | |
| 10,810,850 B2 | 10/2020 | Eckert et al. | |
| 10,928,498 B1 | 2/2021 | Li et al. | |
| 10,936,880 B2 | 3/2021 | Eronen et al. | |
| 11,004,567 B2 | 5/2021 | Eckert et al. | |
| 11,043,038 B1 | 6/2021 | Ngai et al. | |
| 11,143,743 B2 | 10/2021 | Eckert et al. | |
| 11,163,052 B2 | 11/2021 | Eckert et al. | |
| 11,175,393 B2 | 11/2021 | Eckert et al. | |
| 11,184,738 B1 | 11/2021 | Rigazio et al. | |
| 11,218,800 B2 | 1/2022 | Eckert et al. | |
| 11,240,635 B1 | 2/2022 | Eckert et al. | |
| 11,462,330 B2 | 10/2022 | Eckert et al. | |
| 11,558,717 B2 | 1/2023 | Rigazio et al. | |
| 2005/0154929 A1 | 7/2005 | Ahrens et al. | |
| 2006/0053110 A1 | 3/2006 | Mcdonald et al. | |
| 2006/0152404 A1 | 7/2006 | Fullerton et al. | |
| 2006/0284791 A1 | 12/2006 | Chen et al. | |
| 2007/0205937 A1 | 9/2007 | Thompson et al. | |
| 2007/0297695 A1 | 12/2007 | Aratani et al. | |
| 2009/0167862 A1 | 7/2009 | Jentoft et al. | |
| 2009/0224963 A1 | 9/2009 | Nakanishi | |
| 2009/0264715 A1 | 10/2009 | Auphan | |
| 2010/0026479 A1 | 2/2010 | Tran | |
| 2010/0048256 A1 | 2/2010 | Huppi et al. | |
| 2010/0141506 A1 | 6/2010 | Gulden et al. | |
| 2010/0152600 A1 | 6/2010 | Droitcour et al. | |
| 2010/0321229 A1 | 12/2010 | Dwelly et al. | |
| 2011/0077758 A1 | 3/2011 | Tran et al. | |
| 2011/0187816 A1 | 8/2011 | Shimizu | |
| 2011/0190594 A1 | 8/2011 | Heit et al. | |
| 2011/0242305 A1 | 10/2011 | Peterson et al. | |
| 2012/0062729 A1 | 3/2012 | Hart et al. | |
| 2012/0065944 A1 | 3/2012 | Nielsen et al. | |
| 2012/0275236 A1 | 11/2012 | Hess et al. | |
| 2013/0053653 A1 | 2/2013 | Cuddihy et al. | |
| 2014/0022940 A1 | 1/2014 | Apte et al. | |
| 2014/0155705 A1* | 6/2014 | Papadopoulos | A61B 5/1112 600/301 |
| 2014/0207292 A1 | 7/2014 | Ramagem et al. | |
| 2014/0316261 A1 | 10/2014 | Lux et al. | |
| 2014/0375521 A1 | 12/2014 | Andujar Linares et al. | |
| 2015/0079809 A1 | 3/2015 | Silva et al. | |
| 2015/0233598 A1 | 8/2015 | Shikii et al. | |
| 2015/0238137 A1 | 8/2015 | Eyal et al. | |
| 2015/0245167 A1 | 8/2015 | Bobrow et al. | |
| 2015/0265922 A1 | 9/2015 | Yamane et al. | |
| 2015/0286948 A1 | 10/2015 | Luca et al. | |
| 2015/0301167 A1 | 10/2015 | Sentelle et al. | |
| 2015/0302323 A1 | 10/2015 | Connolly | |
| 2015/0310726 A1 | 10/2015 | Sager et al. | |
| 2016/0055332 A1 | 2/2016 | Jeansonne et al. | |
| 2016/0151603 A1 | 6/2016 | Shouldice et al. | |
| 2016/0249021 A1 | 8/2016 | Mcaleenan et al. | |
| 2016/0337441 A1 | 11/2016 | Bloomquist et al. | |
| 2016/0360362 A1 | 12/2016 | Do et al. | |
| 2016/0377705 A1 | 12/2016 | Zack et al. | |
| 2017/0005958 A1 | 1/2017 | Frenkel et al. | |
| 2017/0038456 A1 | 2/2017 | Smith | |
| 2017/0108581 A1 | 4/2017 | Morley | |
| 2017/0328995 A1 | 11/2017 | Marschalkowski et al. | |
| 2018/0012080 A1 | 1/2018 | Glaser et al. | |
| 2018/0031374 A1 | 2/2018 | Hepler et al. | |
| 2018/0050800 A1 | 2/2018 | Boykin et al. | |
| 2018/0143320 A1 | 5/2018 | Steever et al. | |
| 2018/0204470 A1 | 7/2018 | Rezvani et al. | |
| 2018/0295535 A1 | 10/2018 | Kavars et al. | |
| 2018/0351775 A1 | 12/2018 | Zhang et al. | |
| 2018/0357871 A1 | 12/2018 | Siminoff | |
| 2019/0019295 A1 | 1/2019 | Lehtiniemi et al. | |
| 2019/0033440 A1 | 1/2019 | Boolos et al. | |
| 2019/0043466 A1 | 2/2019 | Masterson et al. | |
| 2019/0053707 A1 | 2/2019 | Lane et al. | |
| 2019/0057777 A1 | 2/2019 | Joshi et al. | |
| 2019/0072669 A1 | 3/2019 | Duque Biarge et al. | |
| 2019/0088098 A1 | 3/2019 | Gangumalla et al. | |
| 2019/0108913 A1 | 4/2019 | Coke et al. | |
| 2019/0158494 A1 | 5/2019 | Nakayama et al. | |
| 2019/0159960 A1 | 5/2019 | Nakata et al. | |
| 2019/0197866 A1 | 6/2019 | Mukundala et al. | |
| 2019/0207650 A1 | 7/2019 | Kearney et al. | |
| 2019/0219403 A1 | 7/2019 | Hu | |
| 2019/0278555 A1 | 9/2019 | Carvajal et al. | |
| 2019/0279479 A1 | 9/2019 | Reunamaki et al. | |
| 2019/0289417 A1 | 9/2019 | Tomlin et al. | |
| 2019/0347925 A1 | 11/2019 | Faltaous et al. | |
| 2019/0372363 A1 | 12/2019 | Cutcher et al. | |
| 2019/0375103 A1 | 12/2019 | Cui et al. | |
| 2020/0053574 A1 | 2/2020 | Hasan et al. | |
| 2020/0054236 A1 | 2/2020 | Qi et al. | |
| 2020/0079363 A1 | 3/2020 | Frederick et al. | |
| 2020/0088870 A1 | 3/2020 | Tsiklauri et al. | |
| 2020/0097006 A1 | 3/2020 | Liu et al. | |
| 2020/0097092 A1 | 3/2020 | Tzadok | |
| 2020/0103486 A1 | 4/2020 | Knaappila | |
| 2020/0103513 A1 | 4/2020 | Knaappila | |
| 2020/0103516 A1 | 4/2020 | Kim et al. | |
| 2020/0143123 A1 | 5/2020 | Shen et al. | |

(56) References Cited

U.S. PATENT DOCUMENTS

| | | | |
|---|---|---|---|
| 2020/0158819 | A1 | 5/2020 | Joshi et al. |
| 2020/0158849 | A1 | 5/2020 | Joshi et al. |
| 2020/0168339 | A1 | 5/2020 | Correnti |
| 2020/0196110 | A1 | 6/2020 | Jakobsson |
| 2020/0204541 | A1 | 6/2020 | Nair et al. |
| 2020/0234030 | A1 | 7/2020 | Baheti et al. |
| 2020/0256972 | A1 | 8/2020 | Eckert et al. |
| 2020/0260180 | A1 | 8/2020 | Eckert et al. |
| 2020/0264278 | A1 | 8/2020 | Eckert et al. |
| 2020/0265698 | A1 | 8/2020 | Eckert et al. |
| 2020/0271747 | A1 | 8/2020 | Wu et al. |
| 2020/0272268 | A1 | 8/2020 | Shin et al. |
| 2020/0310749 | A1 | 10/2020 | Miller et al. |
| 2020/0397310 | A1 | 12/2020 | Gu et al. |
| 2021/0033724 | A1 | 2/2021 | Zhang et al. |
| 2021/0035425 | A1 | 2/2021 | Eckert et al. |
| 2021/0037315 | A1 | 2/2021 | Eckert et al. |
| 2021/0046650 | A1 | 2/2021 | Deyle et al. |
| 2021/0063214 | A1 | 3/2021 | Li et al. |
| 2021/0065891 | A1 | 3/2021 | Li et al. |
| 2021/0096216 | A1 | 4/2021 | Rigazio et al. |
| 2021/0150873 | A1 | 5/2021 | Shouldice et al. |
| 2021/0197834 | A1 | 7/2021 | Shaker et al. |
| 2021/0233539 | A1 | 7/2021 | Wexler et al. |
| 2021/0249140 | A1 | 8/2021 | Eckert et al. |
| 2021/0358637 | A1 | 11/2021 | Devdas |
| 2021/0360344 | A1 | 11/2021 | Eckert et al. |
| 2021/0377657 | A1 | 12/2021 | Cnaan et al. |
| 2022/0016519 | A1 | 1/2022 | Van Der Steen et al. |
| 2022/0046388 | A1 | 2/2022 | Rigazio et al. |
| 2022/0051677 | A1 | 2/2022 | Park et al. |
| 2022/0075051 | A1 | 3/2022 | Woo et al. |
| 2022/0076844 | A1 | 3/2022 | Eckert et al. |
| 2022/0091248 | A1 | 3/2022 | Eckert et al. |
| 2022/0182791 | A1 | 6/2022 | Eckert et al. |
| 2022/0236395 | A1 | 7/2022 | Eckert et al. |
| 2023/0092688 | A1 | 3/2023 | Rigazio et al. |

FOREIGN PATENT DOCUMENTS

| | | |
|---|---|---|
| KR | 101536249 B1 | 7/2015 |
| WO | WO-2016193972 A2 | 12/2016 |
| WO | WO-2020102813 A1 | 5/2020 |
| WO | WO-2023018731 A1 | 2/2023 |

OTHER PUBLICATIONS

"U.S. Appl. No. 16/588,755, Final Office Action dated Dec. 6, 2022", 10 pgs.

"U.S. Appl. No. 17/499,510, 312 Amendment filed Dec. 2, 2022", 5 pgs.

"U.S. Appl. No. 17/499,510, Notice of Allowance dated Nov. 18, 2022", 9 pgs.

"U.S. Appl. No. 17/499,510, PTO Response to Rule 312 Communication dated Dec. 6, 2022", 1 page.

"International Application Serial No. PCT/US2019/062043, International Preliminary Report on Patentability dated May 27, 2021", 7 pgs.

"International Application Serial No. PCT/US2019/062043, International Search Report dtaed Mar. 19, 2020", 3 pgs.

"International Application Serial No. PCT/US2019/062043, Written Opinion dated Mar. 19, 2020", 5 pgs.

"International Application Serial No. PCT/US2022/039857, Invitation to Pay Additional Fees dated Oct. 20, 2022", 2 pgs.

Chen, et al., "Google Translation of CN207869389", (Sep. 2018), 5 pgs.

Ganis, "A Portable 3D Imaging FMCW MIMO Radar Demonstrator with a 24x24 Antenna Array for Medium Range Applications", (2018), 15 pgs.

Hannun, Awni, et al., "Sequence-tosequence speech recognition with time-depth separable convolutions", arXiv:1904.02619, (Apr. 2019), 5 pgs.

He, Kaiming, et al., "Deep Residual Learning for Image Recognition", arXiv preprint, arXiv:1512.03385v1 [cs.CV], (Dec. 10, 2015), 12 pgs.

Khan, et al., "A Detailed Algorithm for Vital Sign Monitoring of a Stationary/Non-Stationary Human Through IR-UWB Radar", Sensors 2017, (Feb. 4, 2017), 15 pgs.

Lee, "Design and Performance of a 24-GHz Switch-Antenna Array FMCW Radar System for Automotive Applications", (2010), 8 pgs.

Lien, Jaime, et al., "Soli: Ubiquitous Gesture Sensing with Millimeter Wave Radar", ACM Transactions on Graphics (TOG), vol. 35 Issue 4, Article 142, (Jul. 2016), 19 pgs.

Rahman, Tauhidur, et al., "A Contactless Unobtrusive Sleep Sensing System Using Short-Range Doppler Radar", UBICOMP '15, Osaka, Japan, (Sep. 7-11, 2015), 12 pgs.

Ravanelli, M, et al., "Speech and Speaker Recognition from Raw Waveform with SincNet", arXiv:1812.05920v2, (Feb. 15, 2019), 5 pgs.

Sherman, "AN/FPS-115 PAVE PAWS Radar", (2000), 4 pgs.

Suzuki, et al., "An Approach to a Non-Contact Vital Sign Monitoring Using Dual-Frequency Microwave Radars for Elderly Care", J. Biomedical Science and Engineering 6, (2013), 704-711.

Tian, Yonglong, "RF-Based Fall Monitoring Using Convolutional Neural Networks", Proc. ACM Interact. Mob. Wearable Ubiquitous Technol., vol. 2, No. 3, Article 137, (Sep. 2018), 24 pgs.

Tokoro, S, et al., "Electronically scanned millimeter-wave radar for pre-crash safety and adaptive cruise control system", In IEEE IV2003 Intelligent Vehicles Symposium, (Jun. 2003), 6 pgs.

Wang, Zhihua, et al., "A Review of Wearable Technologies for Elderly Care that Can Accurately Track Indoor Position, Recognize Physical Activities and Monitor Vital Signs in Real Time", (Feb. 10, 2017), 36 pgs.

Yang, et al., "Vital Sign and Sleep Monitoring Using Millimeter Wave", ACM Transactions on Sensor Networks, vol. 13, No. 2, Artical 14, (Apr. 2017), 32 pgs.

"U.S. Appl. No. 16/588,755, Examiner Interview Summary dated Feb. 8, 2023", 2 pgs.

"U.S. Appl. No. 16/588,755, Notice of Allowance dated Mar. 15, 2023", 8 pgs.

"U.S. Appl. No. 16/588,755, Response filed Mar. 3, 2023 to Final Office Action dated Dec. 6, 2022", 8 pgs.

"U.S. Appl. No. 17/074,053, Advisory Action dated Feb. 10, 2023", 4 pgs.

"U.S. Appl. No. 17/074,053, Examiner Interview Summary dated Feb. 3, 2023", 2 pgs.

"U.S. Appl. No. 17/074,053, Response filed Feb. 1, 2023 to Final Office Action dated Nov. 1, 2022", 10 pgs.

"International Application Serial No. PCT/US2022/039857, International Search Report dated Jan. 3, 2023", 3 pgs.

"International Application Serial No. PCT/US2022/039857, Written Opinion dated Jan. 3, 2023", 5 pgs.

"U.S. Appl. No. 16/279,949, Non Final Office Action dated Apr. 21, 2023", 16 pgs.

"U.S. Appl. No. 16/588,755, 312 Amendment filed Apr. 24, 2023", 5 pgs.

"U.S. Appl. No. 16/588,755, PTO Response to Rule 312 Communication dated May 5, 2023", 2 pgs.

"U.S. Appl. No. 17/074,053, Non Final Office Action dated May 1, 2023", 22 pgs.

"U.S. Appl. No. 17/074,053, Response filed Apr. 3, 2023 to Advisory Action dated Apr. 3, 2023", 9 pgs.

"U.S. Appl. No. 17/388,688, Restriction Requirement dated May 1, 2023", 5 pgs.

"U.S. Appl. No. 17/551,587, Examiner Interview Summary dated May 9, 2023", 2 pgs.

"U.S. Appl. No. 17/551,587, Non Final Office Action dated Apr. 14, 2023", 44 pgs.

"U.S. Appl. No. 17/551,587, Response filed May 10, 2023 to Non Final Office Action dated Apr. 14, 2023", 9 pgs.

"U.S. Appl. No. 18/072,315, Examiner Interview Summary dated May 1, 2023", 2 pgs.

"U.S. Appl. No. 18/072,315, Non Final Office Action dated Mar. 21, 2023", 11 pgs.

(56) References Cited

OTHER PUBLICATIONS

"U.S. Appl. No. 18/072,315, Notice of Allowance dated May 5, 2023", 9 pgs.
"U.S. Appl. No. 18/072,315, Response filed Apr. 27, 2023 to Non Final Office Action dated Mar. 21, 2023", 6 pgs.

* cited by examiner

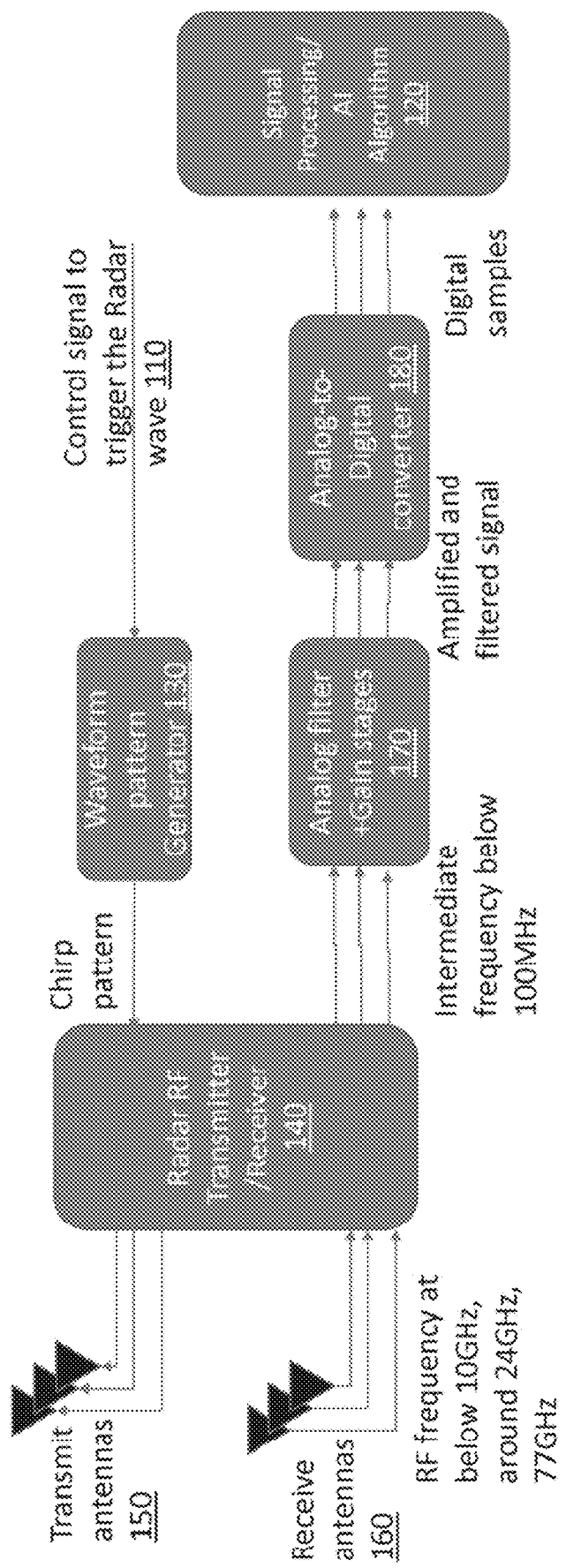

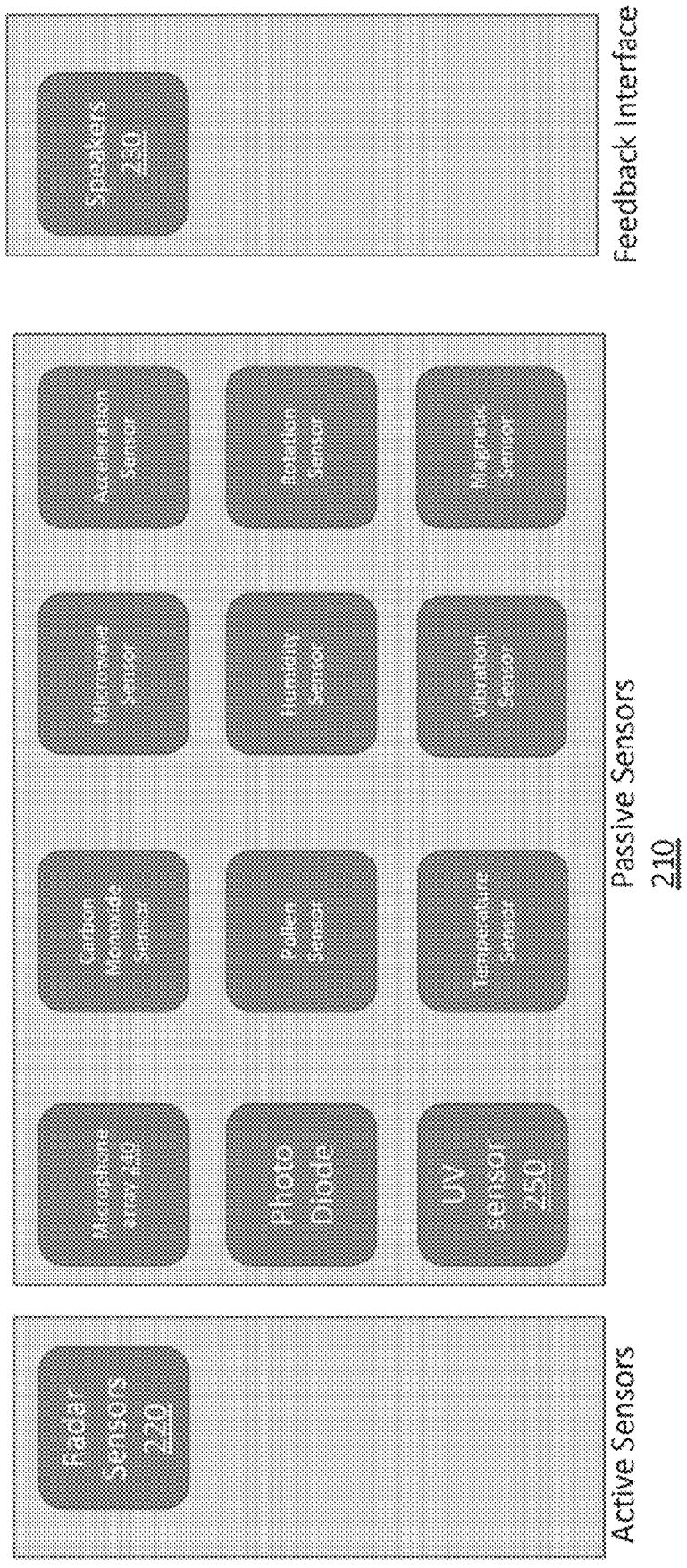

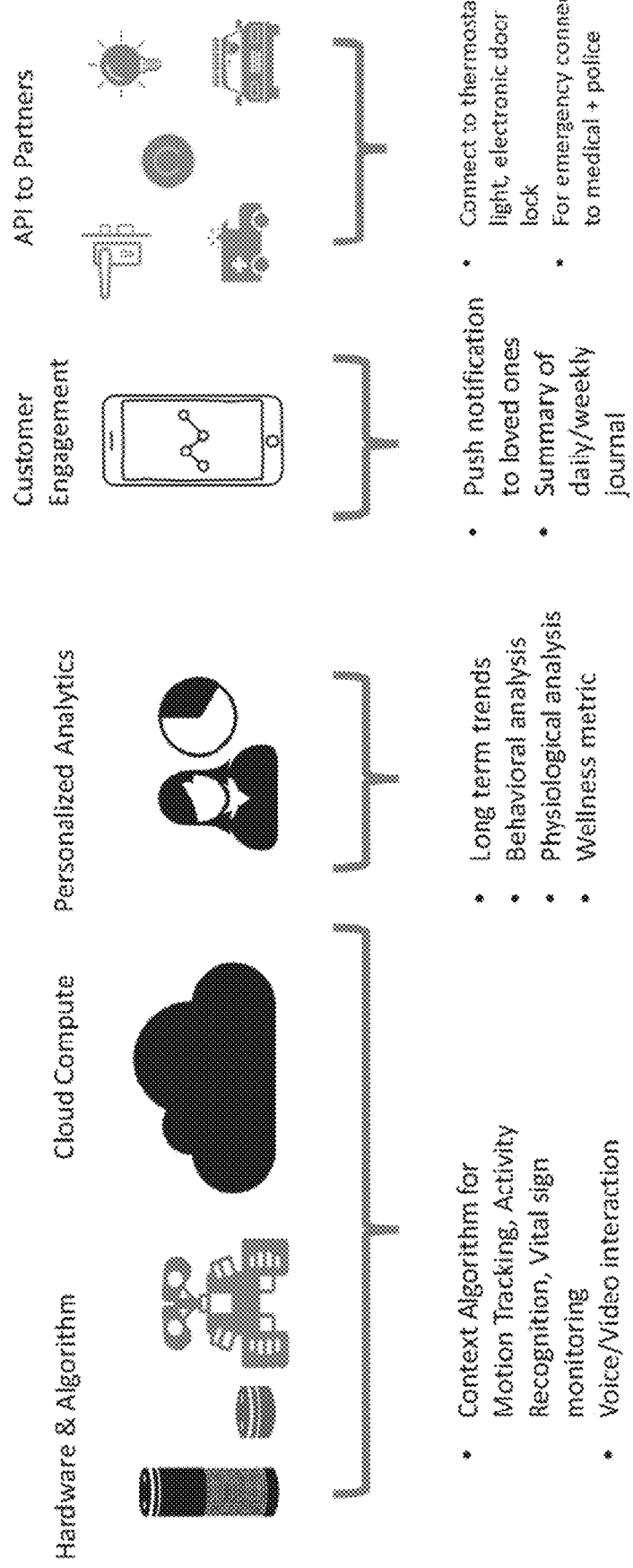

Figure 4: Hardware Units of ADL/Security System

1) Hub
What does it do?
- Activity + vital recognition
- Act as a controller for all other hardware units
- Aggregates sensor data from all units to understand the global context
- Gateway to internet Where? Place it in a central location of house How? Radar, Camera, WiFi receivers, microphone, speaker, pressure, temp, carbon mono, UV

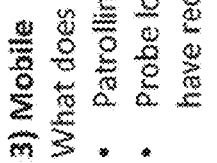

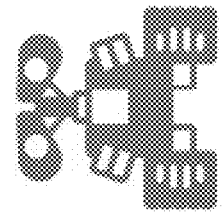

2) Node
What does it do?
- Activity + vital recognition
- Understands the local context and pass that info to Hub Where? Place it near areas where certain critical events are likely to happen

3) Mobile
What does it do?
- Patrolling
- Probe locations where the static units have recognized interesting events Where? It's mobile, will be continuously move around the house How? Radar, Camera, WiFi receivers, microphone, speaker, Inertial (Gyro, Accelerometer, Compass), temp, UWB

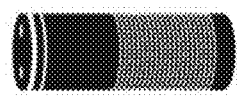
Figure 5: Hub

Figure 9: Mobile Node

Figure 11: Categories of Senior ADL

- Basic ADLs:
  - Bathing
  - Brushing teeth
  - Dressing
  - Using Toilet
  - Eating and Drinking
  - Sleeping
- Instrumented ADLs
  - Preparing meals
  - Preparing drinks
  - Resting
  - Housekeeping
  - Using a telephone
  - Taking medicine
- Ambulatory Activities
  - Walking:
  - Doing Exercise : Running, cycling
  - Transitional Activities : Sit-to-stand, sit-to-lie, stand-to-sit, lie-to-sit in and out of bed or chair
  - Stationary Activities : sits in sofa, stand for a while, lie in bed or sofa Figure 12: Activities List

- Going Out
- Preparing Breakfast
- Having Breakfast
- Preparing Lunch
- Having Lunch
- Preparing Dinner
- Having Dinner
- Washing Dishes
- Having Snack
- Sleeping
- Watching TV
- Studying
- Having Shower
- Toileting
- Having Nap
- Using Internet
- Reading Book
- Shaving
- Brushing Teeth
- Telephone
- Listening Music
- Doing Cleaning
- Having Conversation
- Entertain Guest

SYSTEM AND METHOD FOR PROCESSING WIRELESS BACKSCATTERED SIGNAL USING ARTIFICIAL INTELLIGENCE PROCESSING FOR ACTIVITIES OF DAILY LIFE

CROSS-REFERENCE TO RELATED APPLICATION

The present application is a continuation of U.S. patent application Ser. No. 17/526,283, filed Nov. 15, 2021, which application is a continuation of U.S. patent application Ser. No. 17/244,554, filed Apr. 29, 2021 which is a continuation of U.S. patent application Ser. No. 16/103,829 filed Aug. 14, 2018, now U.S. Pat. No. 11,004,567, which is a non-provisional of, and claims the benefit of priority to U.S. Prov. Pat. App. No. 62/545,921 filed Aug. 15, 2017, now expired; the entire contents of each is incorporated herein by reference.

BACKGROUND

The present invention relates to techniques, including a method, and system, for processing signals using artificial intelligence techniques to monitor, detect, and act on activities. In an example, the signals can be from both active and passive sensors, among others. Merely by way of examples, various applications can include daily life, and others.

Various conventional techniques exist for monitoring people within a home or building environment. Such techniques include use of cameras to view a person. Other techniques include a pendant or other sensing device that is placed on the person to monitor his/her movement. Examples include Personal Emergency Response Systems (PERS) devices such as LifeAlert® and Philips® Life-Line—each of which are just panic buttons for seniors to press in case of an emergency. Unfortunately, all of these techniques have limitations. That is, each of these techniques fails to provide a reliable and high quality signal to accurately detect a fall or other life activity of the person being monitored. Many people often forget to wear the pendant or a power source for the pendant runs out. Also, elderly people do not want to look like they are old so often times, elderly people do not wear the pendant.

From the above, it is seen that techniques for identifying and monitoring a person is highly desirable.

SUMMARY

According to the present invention, techniques, including a method, and system, for processing signals using artificial intelligence techniques to monitor, detect, and act on activities are provided. In an example, the signals can be from both active and passive sensors, among others. Merely by way of examples, various applications can include daily life, and others.

In an example, the present invention provides a sensor array in a single box that can be placed in a home or a single box (acting as a base station) that talks to multiple helper sensor boxes distributed throughout a living space of the home. In an example, the sensor array will communicate with a backend server via standard connectivity solutions, such as Wi-Fi, cellular, or others. In an example, the technique uses distributed processing where processing of the data occurs inside the sensor array and in a cloud server. In an example, artificial intelligence (AI) techniques are included. Depending upon the example, the processed data are disseminated to various interested parties (e.g., children of elderly person, care takers, Emergency Medical Response team) via different communication channels, such as smartphone app, SMS, email, voicemail, and other techniques.

In an example, the present invention provides a method of detecting a status of a human being or target. The method includes transferring, using a wireless transmitter, a wireless signal being selected from one or more of a frequency being less than about 10 G Hz, 24 G Hz, 60 G Hz, or 77 G Hz and greater. The method includes capturing a back scattered signal, using an rf antenna, from the wireless signal. The method includes processing the back scattered signal to extract one or more of a direction, signal strength, distance, and other information over a time period. The method includes extracting, using a signal processing process, vital signs of a human, the vital signs including a heart rate, or a respiration rate. The method includes creating a baseline for each of the vital signs. The method includes extracting, using an AI process, a physical activity of the human being. The method includes creating a physical activity base line for the physical activity and determining a confidence level of each of the received vital signals and each of the physical activities. The method includes transferring an alert to another target upon a triggering even based upon the confidence level of each of the received vital signals and each of the physical activities and correlating each vital sign, using an artificial intelligence process, with one or more patterns or the base line for each of the vital signs.

In an example, the present invention provides a system for monitoring and detecting an activity of a human target. The system has a sensor array, the sensor array comprising a plurality of passive sensors. In an example, each of the plurality of passive sensors is spatially disposed in spatial region of a living area. In an example, the system has a wireless backscattering detection system. The wireless backscattering detection system has a control line coupled to a processing device. In an example, the control line is configured with a switch to trigger an initiation of a wireless signal. The detection system has a waveform pattern generator coupled to the control line, an rf transmitter coupled to the waveform pattern generator, a transmitting antenna coupled to the rf transmitter, an rf receiver, an rf receiving antenna coupled to the rf receiver, an analog front end comprising a filter, an analog to digital converter coupled to the analog front end, a signal processing device coupled to the analog to digital converter, and an artificial intelligence module coupled to the signal processing device, and configured to process information associated with a backscattered signal captured from the rf receiving antenna. Further details of each of these elements can be found throughout the present specification and more particularly below.

The above examples and implementations are not necessarily inclusive or exclusive of each other and may be combined in any manner that is non-conflicting and otherwise possible, whether they be presented in association with a same, or a different, embodiment or example or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above examples implementations are illustrative, rather than limiting.

BRIEF DESCRIPTION OF THE DRAWINGS

FIG. 1 is a simplified diagram of a radar/wireless backscattering sensor system according to an example of the present invention.

FIG. 2 is a simplified diagram of a sensor array according to an example of the present invention.

FIG. 3 is a simplified diagram of a system according to an example of the present invention.

FIG. 4 is a detailed diagram of hardware apparatus according to an example of the present invention.

FIG. 5 is a simplified diagram of a hub according to an example of the present invention.

FIG. 11 is a simplified diagram illustrating senor ADL categories in an example.

FIG. 12 is a simplified diagram illustrating an activity list according to an example.

DETAILED DESCRIPTION OF THE EXAMPLES

Figure 6:
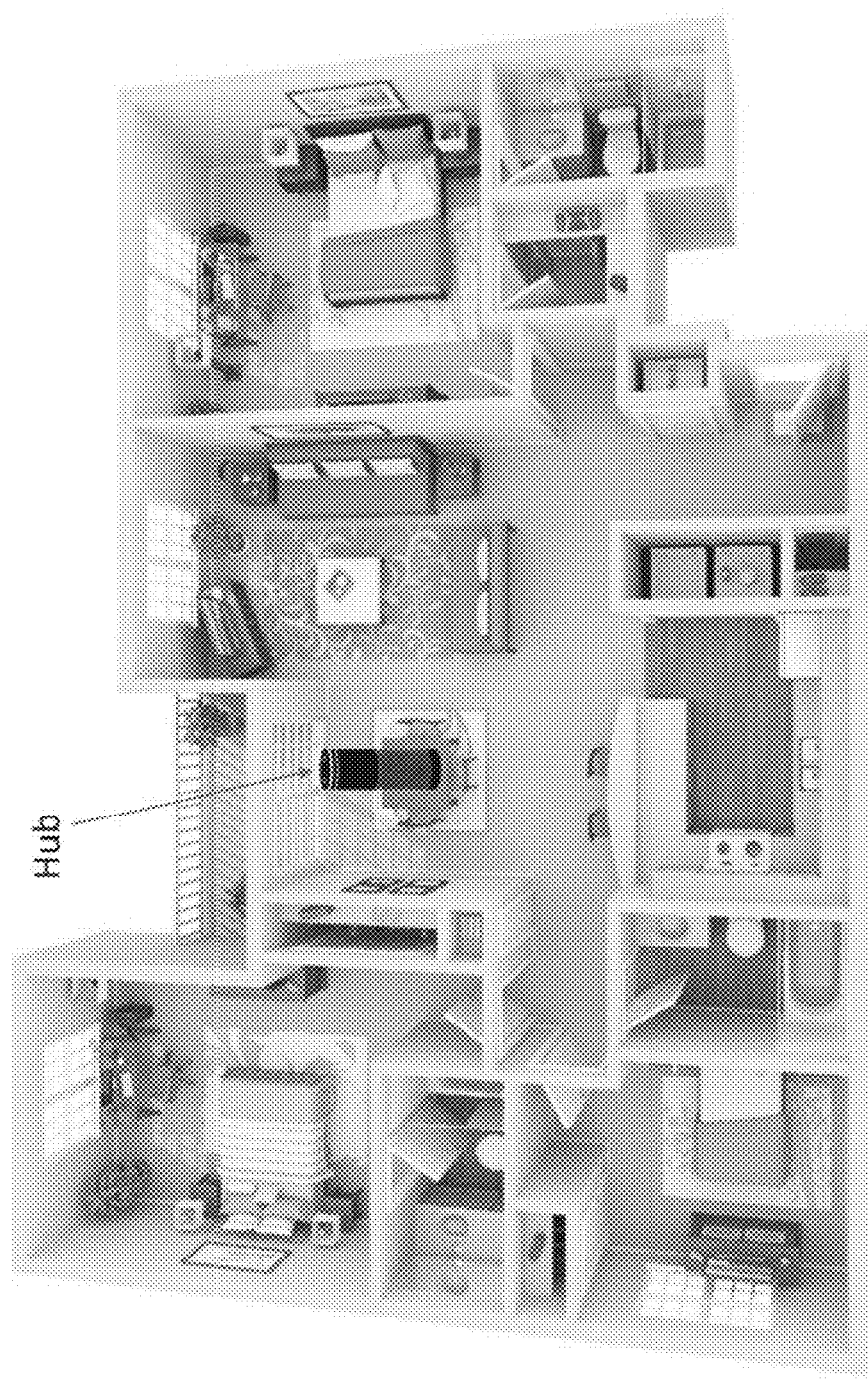
FIG. 6 is a simplified diagram of a hub in a spatial region according to an example of the present invention.

According to the present invention, techniques, including a method, and system, for processing signals using artificial intelligence techniques to monitor, detect, and act on activities are provided. In an example, the signals can be from both active and passive sensors, among others. Merely by way of examples, various applications can include daily life, and others.

FIG. 1 is a simplified diagram of a radar/wireless backscattering sensor system 100 according to an example of the present invention. This diagram is merely an example, which should not unduly limit the scope of the claims herein. In an example, the system is a wireless backscattering detection system. The system has a control line 110 coupled to a processing device 120, the control line being configured with a switch to trigger an initiation of a wireless signal. In an example, the system has a waveform pattern generator 130 coupled to the control line 110. The system has an rf transmitter 140 coupled to the waveform pattern generator 130. The system has transmitting 150 and receiving 160 antennas. In an example, the system has a transmitting antenna 150 coupled to the rf transmitter 140 and an rf receiver 140, which is coupled to an rf receiving antenna 160. In an example, the system has an analog front end 170 comprising a filter. An analog to digital converter 180 coupled to the analog front end 170. The system has a signal-processing device 120 coupled to the analog to digital converter 180. In a preferred example, the system has an artificial intelligence module coupled to the signal-processing device 120. The module is configured to process information associated with a backscattered signal captured from the rf receiving antenna. Further details of the present system can be found through out the specification and more particularly below.

Antenna

In an example, multiple aspects of antenna design can improve the performance of the activities of daily life ("ADL") system. For example, in scanning mode the present technique continuously looks for moving human targets (or user) to extract ADL or fall. Since these can happen anywhere in the spatial region of a home, the present system has antennas that have wide field of view. Once the human target is identified, the technique focuses signals coming only from that particular target and attenuate returns from all other targets. This can be done by first estimating location of the target from our technique using wide field of view antennas and then focusing RF energy on the specific target of interest once it has been identified. In an example, the technique can either electronically switch a different antenna that has narrow field of view or could use beam forming techniques to simultaneously transmit waves from multiple transmit antenna and control their phase such that the RF energy constructively builds around the target of interest where as it destructively cancels everywhere else. This return will be much cleaner and can boost the performance of our ADL+ fall+vital sign sensors.

In another example considers the layout of the antennas itself. In an example, the technique places transmit and receive antennas in various physical configurations (ULA, circular, square, etc.), that can help us establish the direction from which the radar signal returns, by comparing phases of the same radar signal at different receiving antennas. The configurations can play a role because different configurations enable direction of arrival measurement from different dimensions. For example, when the human target falls the vertical angle of arrival changes from top to bottom, therefore a vertical ULA is better suited to capture that information. Likewise during walking horizontal angle of arrival of the signal varies more therefore it makes sense to use horizontal ULA is more sensitive and therefor can provide additional information for our algorithm. Of course, there can be other variations, modifications, and alternatives.

RF Unit

In an example, the wireless RF unit can be either pulsed doppler radar or frequency modulated continuous wave (FMCW) or continuous wave doppler (CW). In an example, on the transmit side it will have standard RF units like VCO, PLL, among others. On the receive side it can have matched filter, LNA, mixer, and other elements. The multiple antennas can be either driven by a single transmit/receive chain by sharing it in time or have one each chain for each of the antennas.

Waveform Unit

In an example, waveform pattern generator generates control signals that define the type of radar signal that is generated by the radar RF unit. For example, for FMCW, it can generate triangular wave of specific slope and period, which will linearly sweep the frequency of the RF unit according to this parameter. For a pulsed doppler radar, the technique will hold generate pulse of specific width and period, which will modulate the RF output accordingly.

Baseband Unit

In an example, the gain and filter stage filters the radar returns to remove any unwanted signals and then amplifies the remaining signal with different techniques. For example, the present artificial intelligence or AI technique can determine what target is desirably tracked and provide feedback to the AI technique, that will filter out radar return from any and all other signals except for the signal that is desirably tracked. If human target is moving the return signal will be fluctuating, in that case, the technique applies automatic gain control (AGC) to find the optimal gain, so that entire dynamic range of ADC in the subsequent stage is satisfied.

In an example, the return signal is converted to digital samples by analog-to-digital converters (ADC), among other front-end elements.

FIG. 2 is a simplified diagram of a sensor array 200 according to an example of the present invention. This diagram is merely an example, which should not unduly limit the scope of the claims herein. Shown is a sensor array. The sensor array includes a plurality of passive sensors 210. In an example, the plurality of passive sensors are spatially disposed in spatial region of a living area. The sensor array has active sensors, such as one or more radar sensors 220. Additionally, the array has a feedback interface, such as a speaker 230 for calling out to a human target in the spatial region of the living area.

In an example, the present technique is provided to identify various activities in home using non-wearable. In an example, the technique is at least privacy intrusive as possible, and will use sensors that are less intrusive. Examples of sensors can include, without limitation, a wireless backscatter (e.g., radar, Wi-Fi), audio (e.g., microphone array, speaker array), video (e.g., PTZ mounted, stereo), pressure mats, infrared, temperature, ultraviolet, humidity, pressure, smoke, any combination thereof, and others.

Active Sensor for RADAR

In an example, the technique can use wireless backscattering to measure motion of human, a location, and an environmental state, such as door opening/closing, or other environmental condition. In an example, the wireless backscattering can also be used to measure a vital sign, such as a heart rate and respiration rate, among others. In an example, the wireless techniques can work in non-line of sight, and is non intrusive compared to camera or microphone, or others. In an example, the technique can use radar\backscatter sensor for two purposes (1) to find the location of an action; and (2) sense different activities associated with the action. Of course, there can be other variations, modifications, and alternatives.

In an example, the present technique and system includes a radar system that operates on multiple frequency bands, such as below 10 GHz, around 24 GHz, 60 GHz, 77-81 GHz, among others. In an example, different frequency interacts differently with various objects in our environment. In an example, available signal bandwidth and permissible signal power are also regulated differently at different frequency hands. In an example, the present techniques optimally combine reflections coming from a reflector from multiple frequency hands to achieve large coverage, and/or improve accuracy. Of course, there can be other variations, modifications, and alternatives.

In an example, each radar is working at a particular frequency band will be using multiple transmit and receive antennas, as shown. In an example, using these multiple transmitters, the technique can perform transmit beam forming to concentrate radar signal on a particular target. In an example, the technique uses multiple receivers to collect reflected signals coming from various reflectors (e.g., human body, walls). After further processing this will allow us to find the direction of the reflector with respect to the radar. In an example, the technique also uses multiple transmitter and receiver to form virtual array, this will allow emulate the radar array with large element by using small number of transmitter and receiver chains. The main benefit is to improve the angle resolution without using a large array, saving space and component cost. In an example, different antenna array configurations to improve coverage (using beam forming) or add 3D localization capability (using 2-D array) are included.

In an example using standard radar signal modulation techniques, such as FMCW/UWB, on MIMO radar, the technique will first separate signals coming from different range and angle. The technique will then identify static reflectors, such as chairs, walls, or other features, from moving ones, such as human targets, pets, or the like. For moving objects that are tracked, the technique will further process signals for each of the reflectors. As an example, the technique will use different techniques to extract raw motion data (e.g., like spectrogram). In an example, the technique will apply various filtering process to extract periodic signals generated by vital signs, such as heart rate, respiration rate, among others. In an example, both the raw motion data and extracted vital signs will be passed to a downstream process, where they are combined with data from other sensors, such as radar outputs operating at different frequency or completely different sensors to extract higher insights about the environment. Of course, there can be other variations, modifications, and alternatives.

Audio Sensor

In an example, the present technique uses a sensor array that has a multiple microphone array 240. In an example, these microphones 240 will be use to ascertain the direction of arrival of any audio signal in the environment. In an example, the microphone 240 in conjunction with other sensors, such as radar 220, will be vital in performing two tasks: 1st it will augment radar signal to identify various activities (walking produces a different sound than sitting), if the target is watching TV it is much easier to ascertain it with audio signal; and 2nd in case of emergency like fall, the technique can use the radar signal to identify the location of the fall and then beam form microphone array towards that location, so that any audio signal produced by the target can be captured. Of course, there can be other variations, modifications, and alternatives.

Sensor Fusion and Soft Sensors

In addition to a radar sensor, which is consider as active sensors the present sensor system (e.g., box, boxes) will also have additional passive sensors that captures the sound, chemical signature, environmental conditions. Each of these of the sensors captures different context about the home that the human being tracking is living in or occupying. In an example, the UV 250 sensor can monitor how often the sunlight comes in the room. In an example, light sensors determine a lighting condition of the human's home or living area.

In an example, a microphone array 240 can have many functions, such as use to sense sound in the room, to figure out how long the human has spent watching TV, or how many time they went to bathroom by listening to the sound of toilet flushing or other audio signature. In an example, the present technique can use creative solutions where it can use the active sensor to find the location of the person and then tune the microphone array to enhance the sound coming from that location only, among other features. In an example, the technique can call the sensors that are derived from the hardware sensors using specific algorithms as software sensors or soft sensors. So the same hardware sensors can be used for many different applications by creating different software sensors. Here the software sensors can combine signals from one or more sensors and then apply sensor fusion and AI techniques to generate the desired output. Of course, there can be other variations, modifications, and alternatives.

Soft Sensor for Detecting Cooking and Eating Habits

In example, radar sensors can determine information about a human's location within a home, like if they are in kitchen area, or other. In an example, when the human target turns on the microphone oven, it generates specific RF signature that can be tracked. In an example, the technique can combine this information to infer if the human target walked to the kitchen and turned on the microphone. Likewise, when the human target prepares food in kitchen he/she can make lot of specific noise like utensils clattering, chopping, or other audio signature. So if a human target goes to kitchen spends sometime in the kitchen, and the present microphone pick these sounds, the technique can infer that food is cooking or other activity.

Soft Sensor for Detecting Bathroom Habits

In an example, toileting frequency can be a very valuable indication of ones wellness. The present technique can track if a human went to the bathroom using the radar or other sensing techniques. In an example, additionally, the technique can pick sound signature of toilet flushing. In an example, the technique combines these two pieces of information, which can be correlated to toileting frequency. In an example, similarly, bathing is a unique activity that requires 4-5 minutes of specific movements. By learning those patterns, the technique can figure out ones bathing routines.

Soft Sensor for Detecting Mobile Habits

In an example, different sensors are triggered by different motion of a human target. In an example, radar can detect human fall by looking at micro doppler patterns generating by different part of the target during falls. In an example, the technique can also simultaneously hear a fall from microphone arrays and vibration sensors. In an example, the technique can also detect how pace of movement changes for an individual over a long duration by monitoring the location information provided by radar or other sensing technique. In an example, likewise, the technique can gather unstable transfers by analyzing the gait of the target. In an example, the technique can find front door loitering by analyzing the radar signal pattern. In an example, the technique can figure out immobility by analyzing the radar return. In this case, the technique can figure out the target's presence by analyzing the target's vital signs, such as respiration rate or heart rate or by keeping track of the bread crumb of the target's location trace.

In any and all of the above cases, the technique can also learn about the exact environmental condition that triggered a particular state. For example, the technique can figure out whether a human target was immobile because the target was watching TV or a video for long duration or the target was simply spending a lot of time in their bed. And these can be used to devise incentives to change the target's behavioral pattern for better living.

Soft Sensor for Detecting Vital Signs

In an example, the technique can estimate vital signs of a person by sensing the vibration of the target's body in response to the breathing or heart beat, each of the actions results in tiny phase change in the radar return signals, which can be detected. In an example, the technique will use several signal processing techniques to extract them. Of course, there can be other variations, modifications, and alternatives.

In an example, different frequency radio wave interact with environment differently. Also phase change due to vital signs (HR, RR) differs by frequency, for example phase change for a 77 GHz radar is much higher than for a 10 GHz radar. Thus 77 GHz is more appropriate for estimating heart-beat more accurately. But higher frequency typically attenuates much more rapidly with distance. Therefore, lower frequency radar can have much larger range. By using multi-frequency radar in the present technique can perform these vital trade-offs.

Soft Sensor for Detecting Sleeping Habits

In an example, the present radar sensors can detect motions that are generated during sleep, such as tossing and turning. In an example, radar sensors can also sense vital signs like respiration rate and heart rate as described earlier. In an example, now combining the pattern of toss and turn and different breathing and heart beat pattern, the technique can effectively monitor the target's sleep. Additionally, the technique can now combine results from passive sensors, such as a thermometer, UV, photo diode, among others, to find correlation between certain sleep pattern and the environmental conditions. In an example, the technique can also use the sleep monitor soft sensor to learn about day/night reversal of sleep, and the associated environmental condition by looking at different passive sensors. In an example, the techniques can be valuable in providing feedback to improve the human target's sleep. For example, the technique can determine or learn that certain environmental condition results in better sleep and prescribe that to improve future sleep.

Soft Sensor for Security Applications

In an example, the technique can repurpose many of the sensors described before for security applications. For a security application, the technique determines where one or more person is located, which can be detected using a presence detection sensor that is build on top of radar signals. In an example, the technique can eliminate one or many false positive triggered by traditional security systems. For example, is a window is suddenly opened by a wind the technique (and system) will look at presence of human in the vicinity before triggering the alarm. Likewise, combination of vital signs, movement patterns, among others, can be used a biometric to identify any human target. If an unknown human target is detected in the vicinity at certain time of the day, the technique can trigger an alarm or alert.

In an example, any one of the above sensing techniques can be combined, separated, or integrated. In an example, n addition to radar and audio sensors, other sensors can be provided in the sensor array. Of course, there can be other variations, modifications, and alternatives.

FIG. 3 is a simplified diagram of a system according to an example of the present invention. This diagram is merely an example, which should not unduly limit the scope of the claims herein. As shown, the system has hardware and method (e.g., algorithm), cloud computing, personalized analytics, customer engagement, and an API to various partners, such as police, medical, and others. Further details of the present system can be found throughout the present specification and more particularly below.

FIG. 4 is a detailed diagram of hardware apparatus according to an example of the present invention. This diagram is merely an example, which should not unduly limit the scope of the claims herein. As shown, the hardware units include at least a hub device, node, and mobile node, each of which will be described in more detail below.

FIG. 5 is a simplified diagram of a hub according to an example of the present invention. This diagram is merely an example, which should not unduly limit the scope of the claims herein. In an example, the hub includes various sensing devices. The sensing devices, include, among others, a radar, a WiFi, a Bluetooth, a Zigbee sniffer, a microphone and speakers, a smoke detector, a temperature detector, a humidity detector, a UV detector, a pressure detector, MEMS (e.g., accelerometer, gyroscope, and compass), a UWB sensors (for finding locations of all the deployed elements relative to each other), among others. In an example, the hub is a gateway to internet via Wi-Fi, GSM, Ethernet, landline, or other technique. The hub also connects to other units (Mini Node/Mobile Node) via Bluetooth, Wi-Fi, Zigbee, UWB and coordinates them with each other. In an example, certain data processing, such as noise removal, feature extraction to reduce amount of data uploaded to cloud is included. In an example, the hub alone can be sufficient to cover a small living space. In an example, the hub is deployed as a single device somewhere in a desirable location (e.g., middle of the living space) so that it has good connectivity to all other units. An example of such deployment is provided in the Figure below.

FIG. 6 is a simplified diagram of a huh in a spatial region according to an example of the present invention. This diagram is merely an example, which should not unduly limit the scope of the claims herein. As shown, the hub is deployed in the middle of the living space in a house.

Figure 7:
FIG. 7 is a simplified diagram of a mini node according to an example of the present invention.

FIG. 7 is a simplified diagram of a mini node according to an example of the present invention. This diagram is merely an example, which should not unduly limit the scope of the claims herein. As shown, the system has sensors, which is a subset of sensors in the hub. The sensors are configured to in various spatial locations to improve coverage area and improve accuracy for detection of critical events (e.g., fall, someone calling for help). The sensors also communicate with the hub via Wi-Fi, Bluetototh, ZigBee or UWB, or other technique. Additionally, the sensors or each mini node is deployed in a bathrooms, where chances of fall is high, a kitchen, where we can learn about eating habits by listening to sounds, RF waves, vibrations, or a perimeter of the living space, that will allow us to learn approximate map of the space under consideration, among other locations. Additionally, each of the mini modes can save power and costs by adding more complexity on the hub. This can even enable us to operate on battery for extended periods. For example, each of the nodes can have only single antenna Wi-Fi and hub could have multiple antennas, for WiFi based sensing. Additionally, each of the nodes use simpler radar (e.g., single antenna doppler) vs MIMO FMCW in the HUB. Additionally, each node can be configured with a single microphone whereas the hub can have array of microphone. Of course, there can be other variations, modifications, and alternatives.

Figure 8:
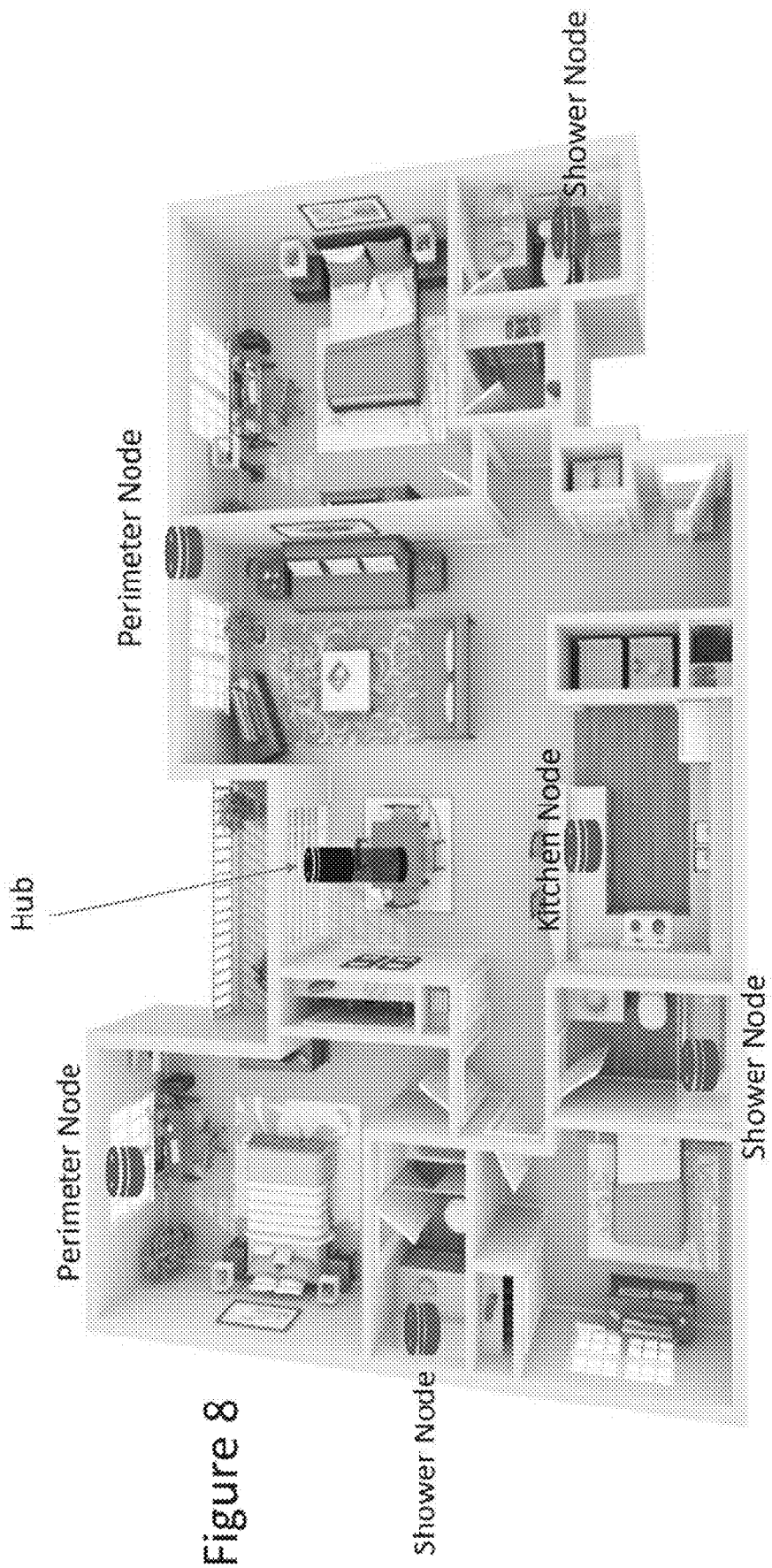
FIG. 8 is a simplified diagram of a mini mode in a spatial region according to an example of the present invention.

FIG. 8 is a simplified diagram of a mini mode in a spatial region according to an example of the present invention. This diagram is merely an example, which should not unduly limit the scope of the claims herein. As shown, each node is configured in a kitchen, shower, perimeter, or other location.

Figure 9:
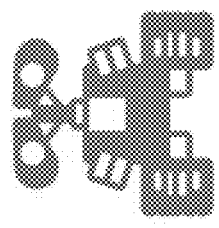
FIG. 9 is a simplified diagram of a mobile node according to an example of the present invention.

FIG. 9 is a simplified diagram of a mobile node according to an example of the present invention. This diagram is merely an example, which should not unduly limit the scope of the claims herein. In an example, each mobile node is a subset of sensors in the hub. The mobile node sensors include a camera such as RGB or IR. In an example, each of the nodes and hub collaboratively figure out interesting events, and pass that information to the mobile node. The technique then goes to the location and probes further. In an example, the camera can be useful to visually find what is going on in the location. In an example, freewill patrolling can be use to detect anything unusual or to refine details of the map created based on perimeter nodes. In an example, onboard UWB can enable precise localization of the mobile node, which can also enable wireless tomography, where the precise RGB and wireless map of the living space is determined.

Figure 10:
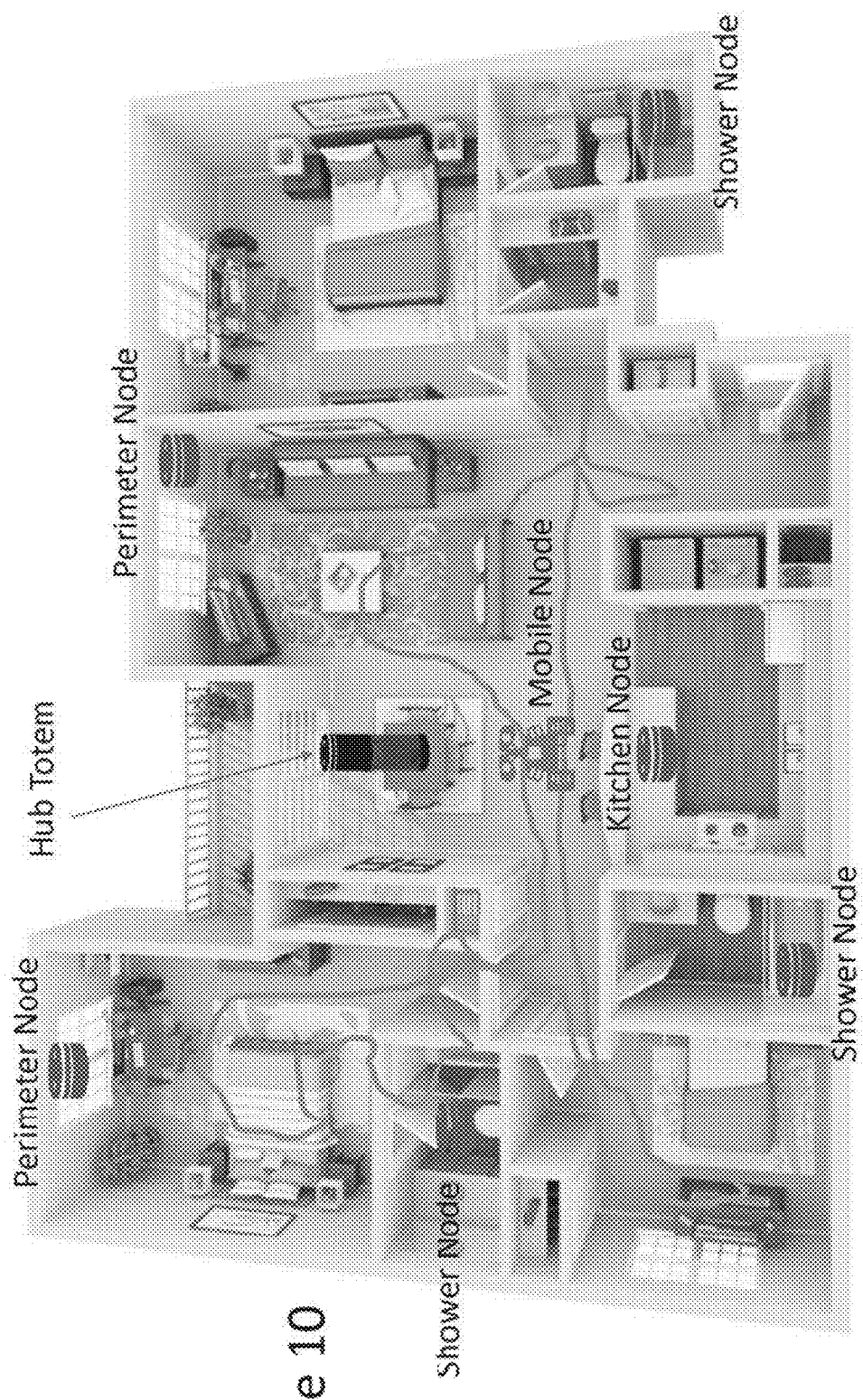
FIG. 10 is a simplified diagram of a mobile mode in a spatial region according to an example of the present invention.

FIG. 10 is a simplified diagram of a mobile mode in a spatial region according to an example of the present invention. This diagram is merely an example, which should not unduly limit the scope of the claims herein. As show, the mobile node, such as a mobile phone or smart phone or other movable device, can physically move throughout the spatial location. The mobile node can also be a drone or other device.

In an example, the technique transfers learned information and activity information to third parties. The technique teaches itself to learn high level behavior that are indicative of a person's welfare using artificial intelligence techniques. in an example, the present technique will then generate summary of such activities and send it out to the human's loved ones, caretaker or even emergency response team depending on the urgency of the situation. For example, for regular days, the technique can simply send short summary like "your mom had a routine activity today", or "She was much less active today." In an example, where the human has a care taker visiting few times a week, the technique can send a notification to them, "It seems she struggles more on yesterday", so that the care taker can pay a visit to make sure everything is fine. Alternatively, the technique can be more acute events like fall, shortness of breathing, or others, that needs quick attention. In these scenarios, the technique can notify medical response team to provide immediate help. Of course, there can be other variations, modifications, and alternatives.

FIG. 11 is a simplified diagram illustrating senor ADL categories in an example. As shown, the present technique can categorize a human target with the listed ADLs, among others.

FIG. 12 is a simplified diagram illustrating an activity list according to an example. As shown, the present technique can determine activities of a human target with any one of the activities listed.

In an example, the present technique can also identify a rare event. In an example, the technique identifies when a senior human falls inside a home with no one around. In an example, the technique is robust, without any false negatives. In an example, the technique uses looking at sequence of events that are before to the potential fall and after a potential fall. In an example, the technique combines the contextual information to robustly determine if a fall has occurred. Of course, there can be other variations, modifications, and alternatives.

In an example, the technique also detects and measures vital signs of each human target by continuous, non-intrusive method. In an example, the vital signs of interest include a heart rate and a respiratory rate, which can provide valuable information about the human's wellness. Additionally, the heart rate and respiratory rate can also be used to identify a particular person, if more than two target humans living in a home. Of course, there can be other variations, modifications, and alternatives.

By understanding the context of how the target human (e.g., elderly) is doing, the technique can also provide valuable feedback directly to the elderly using a voice interface. For example, the technique can sense a mood of the human based on sequence of activities and vital signs of the human and then ask, "Hi do you want me to call your son". Based upon the feedback from the human, the technique can help connect to a third party (or loved one) if their answer is positive. Of course, there can be other alternatives, variations, and modifications.

Having described various embodiments, examples, and implementations, it should be apparent to those skilled in the relevant art that the foregoing is illustrative only and not limiting, having been presented by way of example only. Many other schemes for distributing functions among the various functional elements of the illustrated embodiment or example are possible. The functions of any element may be carried out in various ways in alternative embodiments or examples.

Also, the functions of several elements may, in alternative embodiments or examples, be carried out by fewer, or a single, element. Similarly, in some embodiments, any functional element may perform fewer, or different, operations than those described with respect to the illustrated embodiment or example. Also, functional elements shown as distinct for purposes of illustration may be incorporated within other functional elements in a particular implementation. Also, the sequencing of functions or portions of functions generally may be altered. Certain functional elements, files, data structures, and so one may be described in the illustrated embodiments as located in system memory of a particular or hub. In other embodiments, however, they may be located on, or distributed across, systems or other platforms that are co-located and/or remote from each other. For example, any one or more of data files or data structures described as co-located on and "local" to a server or other computer may be located in a computer system or systems remote from the server. In addition, it will be understood by those skilled in the relevant art that control and data flows between and among functional elements and various data structures may vary in many ways from the control and data flows described above or in documents incorporated by reference herein. More particularly, intermediary functional elements may direct control or data flows, and the functions of various elements may be combined, divided, or otherwise rearranged to allow parallel processing or for other reasons. Also, intermediate data structures of files may be used and various described data structures of files may be combined or otherwise arranged.

In other examples, combinations or sub-combinations of the above disclosed invention can be advantageously made. Some embodiments may incorporate smart speaker interface and controls, such as currently provided by Google Home, Amazon Alexa, Apple HomePod and others. For example, using the sensor and AI techniques described above, the device may perform appropriate actions. As examples of this, if the device determines that the user has fallen down and cannot get up, the device may call for help, turn on all the lights, and/or unlock the doors; if the device determines that the user is cooking, the device may turn on an exhaust fan, increase sensitivity for a smoke detector, and/or turn on the lights in the kitchen; if the device determines that the user is alone watching television, the device may turn off lights in other rooms; turn down the light in the room the user is in; and turn off music playing in other rooms; and the like. In light of the present disclosure, one of ordinary skill in the art should recognize many other types of actions that may be performed based upon the user sensed activity.

The block diagrams of the architecture and flow charts are grouped for ease of understanding. However it should be understood that combinations of blocks, additions of new blocks, re-arrangement of blocks, and the like are contemplated in alternative embodiments of the present invention. Further examples of embodiments of the present invention are provided in the attached appendix.

Examples of processing techniques can be found in Exhibit 1, which is incorporated by reference herein.

The specification and drawings are, accordingly, to be regarded in an illustrative rather than a restrictive sense. It will, however, be evident that various modifications and changes may be made thereunto without departing from the broader spirit and scope of the invention as set forth in the claims.

The invention claimed is:

1. A system configured for sleep monitoring of an individual and improvement of a sleep of the individual, the system comprising:
   (a) a hub disposed in a living space;
   (b) a sensor disposed in the hub and configured to capture data from the individual, the data related to the sleep of the individual, wherein the sensor is configured to sense one or more of a heart rate of the individual, a breathing of the individual, and a movement of the individual, and
   wherein the sensor is configured to capture the data from the individual without the hub contacting the individual; and
   (c) software configured to process the data to generate an evaluation of the sleep of the individual, and wherein the software is further configured to provide a behavioral feedback to the individual based on the evaluation of the sleep of the individual that modifies a behavior of the individual that affects the sleep of the individual when the behavioral feedback is followed by the individual, resulting in the improvement of the sleep of the individual.

2. The system of claim 1, wherein the sensor is configured to monitor one or more of a location of the individual and a position of the individual.

3. The system of claim 2, wherein the sensor is configured to provide a context regarding the one or more of the location and the position of the individual.

4. The system of claim 1, wherein the sensor is configured to operate when there is another individual within proximity of the individual, and wherein the sensor is configured to distinguish between data associated with the individual and data associated with the other individual.

5. The system of claim 1, wherein the movement of the individual comprises a tossing and turning of the individual.

6. The system of claim 1, further comprising a sensor configured to measure an environmental factor.

7. The system of claim 6, wherein the software is configured to modify the environmental factor.

8. The system of claim 1, wherein the sensor comprises a microphone.

9. The system of claim 1, wherein the behavioral feedback relates to activities of the individual before or when the individual goes to sleep.

10. The system of claim 1, wherein the hub alone is sufficient to cover the living space.

11. A system for remotely monitoring a status of an individual, comprising:
   (a) a hub disposed in a living space;
   (b) one or more sensors configured to capture data from the individual, the data related to one or more of a location of the individual and a position of the individual, wherein the one or more sensors are coupled with the hub, and wherein the one or more sensors are configured to capture the data from the individual without the hub contacting the individual;
   (c) a processor, wherein the processor only receives location data or position data for the individual from the one or more sensors configured to capture the one or more of the location of the individual and the position of the individual; and (d) software configured to process the data to determine whether the individual has fallen and is in need of assistance, the software further configured to cause the system to notify a third party that the individual has fallen.

12. The system of claim 11, wherein the one or more sensors are disposed within a home of the individual and configured to operate therein.

13. The system of claim 12, wherein the one or more sensors are configured to operate when the individual is positioned behind a wall or an object.

14. The system of claim 11, wherein the one or more sensors are configured to operate when there is another individual within proximity to the individual.

15. The system of claim 14, wherein the software is configured to distinguish between data associated with the individual and the another individual.

16. The system of claim 11, further comprising an audio element configured for voice interaction with the individual when the individual is in need of assistance.

17. The system of claim 11, wherein the one or more sensors are configured to monitor a vital sign of the individual.

18. The system of claim 11, wherein the software is configured to cause the processor to contact emergency services when it is determined that the individual has fallen and is in need of assistance.

19. The system of claim 11, wherein the software is configured to cause the processor to predict a fall of the individual.

20. The system of claim 11, wherein the hub alone is sufficient to cover the living space.

21. A system for monitoring a status of a target human and improving the status of the target human, the system comprising:

(a) a hub disposed in a living space;

(b) one or more sensors configured to capture data from the target human, the data related to one or more activities of daily living of the target human, wherein the one or more sensors are configured to sense one or more of a vital sign of the target human and a movement of the target human, wherein the one or more sensors are disposed in the hub, and wherein the one or more sensors are configured to capture the data from the target human without the hub contacting the target human; and (c) software configured to process the data to generate an evaluation of the status of the target human, and wherein the software is further configured to provide a behavioral feedback or an incentive directly to the target human based on the evaluation of the status of the target human that modifies a behavior of the target human when the behavioral feedback or the incentive is followed by the target human, resulting in better living for the target human.

22. The system of claim 21, wherein the one or more sensors are disposed within a home of the target human and configured to operate therein.

23. The system of claim 21, wherein the one or more sensors are configured to operate when the target human is positioned behind a wall or an object.

24. The system of claim 21, wherein the one or more sensors are configured to operate when there is another individual within proximity to the target human.

25. The system of claim 24, wherein the software is configured to distinguish between data associated with the target human and the another individual.

26. The system of claim 21, further comprising an audio element configured for voice interaction with the target human when the target human is in need of assistance.

27. The system of claim 21, wherein the software is configured to contact emergency services when it is determined that the target human has fallen and is in need of assistance.

28. The system of claim 21, wherein the software is configured to predict a fall of the target human.

29. The system of claim 21, wherein the one or more sensors configured to capture data from the target human are all sensors in the system configured to capture data related to one or more activities of daily living of the target human, and wherein the one or more sensors are disposed in a single housing.

30. The system of claim 21, wherein the hub alone is sufficient to cover the living space.

* * * * *

UNITED STATES PATENT AND TRADEMARK OFFICE
CERTIFICATE OF CORRECTION

| | | |
|---|---|---|
| PATENT NO. | : 11,776,696 B2 | |
| APPLICATION NO. | : 17/883654 | |
| DATED | : October 3, 2023 | |
| INVENTOR(S) | : Eckert et al. | |

It is certified that error appears in the above-identified patent and that said Letters Patent is hereby corrected as shown below:

On the Title Page

On page 3, in Column 1, under "Other Publications", Line 13, delete "dtaed" and insert --dated-- therefor On page 3, in Column 1, under "Other Publications", Line 23, delete "Sequence-tosequence" and insert --"Sequence-to-sequence-- therefor On page 3, in Column 2, under "Other Publications", Line 60, delete "Apr. 3, 2023"," and insert --Feb. 10, 2023",-- therefor In the Specification In Column 2, Line 9, delete "G Hz," and insert --GHz,-- therefor In Column 2, Line 9, delete "G Hz," and insert --GHz,-- therefor In Column 2, Line 9, delete "G Hz," and insert --GHz,-- therefor In Column 2, Line 9, delete "G Hz" and insert --GHz,-- therefor In Column 5, Line 48, delete "hands." and insert --bands.-- therefor In Column 5, Line 50, delete "hands" and insert --bands-- therefor In Column 7, Line 12, after "sometime", insert --time--

In Column 9, Line 17, delete "huh" and insert --hub-- therefor

Signed and Sealed this
Twenty-third Day of January, 2024

*Katherine Kelly Vidal*

Katherine Kelly Vidal
*Director of the United States Patent and Trademark Office*

In Column 9, Line 30, delete "Bluetototh," and insert --Bluetooth,-- therefor

In Column 10, Line 17, delete "in" and insert --In-- therefor